(12) United States Patent
Lindkamp et al.

(10) Patent No.: US 10,090,607 B2
(45) Date of Patent: Oct. 2, 2018

(54) CONNECTION APPARATUS FOR CABLES (71) Applicant: HARTING Electronics GmbH, Espelkamp (DE)

(72) Inventors: Marc Lindkamp, Lübbecke (DE); Hanno Wolff, Nürnberg (DE); Rainer Bussmann, Bad Essen (DE)

(73) Assignee: HARTING Electronics GmbH, Espelkamp (DE)

( * ) Notice: Subject to any disclaimer, the term of this patent is extended or adjusted under 35 U.S.C. 154(b) by 0 days.

(21) Appl. No.: 15/552,967

(22) PCT Filed: Feb. 1, 2016

(86) PCT No.: PCT/DE2016/100043
§ 371 (c)(1),
(2) Date: Aug. 23, 2017

(87) PCT Pub. No.: WO2016/134695
PCT Pub. Date: Sep. 1, 2016

(65) Prior Publication Data
US 2018/0248274 A1 Aug. 30, 2018

(30) Foreign Application Priority Data
Feb. 24, 2015 (DE) .................. 10 2015 102 634

(51) Int. Cl.
*H01R 4/60* (2006.01)
*H01R 4/2433* (2018.01)
(Continued)

(52) U.S. Cl.
CPC ....... *H01R 4/2433* (2013.01); *A61M 16/0816* (2013.01); *A61M 16/1095* (2014.02);
(Continued)

(58) Field of Classification Search
CPC .. H01R 4/2433; H01R 13/501; H01R 13/005; H01R 11/05; H01R 4/20; H01R 2201/12; A61M 16/1095; A61M 16/0816
See application file for complete search history.

(56) References Cited

U.S. PATENT DOCUMENTS 3,576,518 A 4/1971 Bazille, Jr. et al.
4,125,312 A * 11/1978 Aimar .................. H01R 13/516
439/470

(Continued)

FOREIGN PATENT DOCUMENTS

DE 20 2007 013 963 U1 3/2009
DE 20 2007 018 089 U1 6/2009
(Continued)

OTHER PUBLICATIONS

German Office Action, dated Feb. 11, 2016, for German Application No. 10 2015 109 247.6, 7 pages.
(Continued)

*Primary Examiner* — Jean F Duverne
(74) *Attorney, Agent, or Firm* — Seed IP Law Group LLP (57) ABSTRACT

A connection apparatus for electrical cables is provided. In this case, the connection apparatus is intended to engage around a hose, wherein the connection apparatus is formed from two half-shells which are connected to one another in an articulated manner. In addition, at least one contact element, which is designed to make contact with the electrical cables, is arranged on the connection apparatus. The electrical cables can be connected to the contact elements by means of a pressure piece. As an alternative, the contact elements can be arranged such that, when the connection apparatus is locked, the contact elements are connected to the electrical cables at the same time. In this case, the electrical cables in the second half-shell can be arranged in conductor receptacles such that the contact elements on the first half shell enter the connection apparatus when said connection apparatus is closed.

15 Claims, 6 Drawing Sheets

(51) Int. Cl.
*H01R 4/20* (2006.01)
*H01R 11/05* (2006.01)
*H01R 13/00* (2006.01)
*A61M 16/08* (2006.01)
*A61M 16/10* (2006.01)
*H01R 13/50* (2006.01)
*A61M 39/10* (2006.01)

(52) U.S. Cl.
CPC ............... *H01R 4/20* (2013.01); *H01R 11/05* (2013.01); *H01R 13/005* (2013.01); *H01R 13/501* (2013.01); *A61M 2039/1022* (2013.01); *H01R 2201/12* (2013.01)

(56) References Cited

U.S. PATENT DOCUMENTS

| | | | | |
|---|---|---|---|---|
| 4,466,677 | A * | 8/1984 | Lyman | H01R 13/005 439/192 |
| 4,894,021 | A | 1/1990 | Holden et al. | |
| 6,884,122 | B2 * | 4/2005 | Robinson | A61N 1/3752 439/722 |
| 7,614,911 | B2 * | 11/2009 | Hsieh | H01R 13/5845 174/135 |
| 8,813,629 | B1 * | 8/2014 | Holmes | F41A 3/06 89/18 |
| 8,925,573 | B2 | 1/2015 | Borgmeier et al. | |
| 2014/0236083 | A1 | 8/2014 | Sims | |

FOREIGN PATENT DOCUMENTS

| | | |
|---|---|---|
| DE | 11 2014 005 919 A1 | 11/2014 |
| JP | 6-58467 A | 3/1994 |
| WO | 99/60669 A1 | 11/1999 |

OTHER PUBLICATIONS

German Office Action, dated Jun. 14, 2017, for German Application No. 10 2015 109 247.6, 5 pages.
International Search Report and Written Opinion, dated May 2, 2016, for International Application No. PCT/DE2016/100043, 10 pages. (with English Translation of Search Report).

* cited by examiner

CONNECTION APPARATUS FOR CABLES

BACKGROUND

Technical Field

This disclosure relates to a connection apparatus for electrical cables.

Description of the Related Art

This disclosure relates to a connection device for electrical cables, comprising a sleeve-like holding element and at least one contact element, wherein the holding element is formed from a first half-shell and a second half-shell. The first half-shell and the second half-shell are joined to each other via a hinged joint, wherein the first half-shell and the second half-shell have a locking device on the side situated opposite the hinged joint.

Such a connection element is required to electrically contact electrical cables or lines which are arranged about a cylindrical component, such as, for example, a hose for artificially ventilating patients in the field of medicine. It must be possible to heat such hoses so that the air conveyed is prewarmed in the hose. This is required in order to provide a patient with air or oxygen at body temperature; otherwise there is a possibility of colds, inflammation of the lungs, or similar illnesses caused by the supply of oxygen that is too cold.

For this purpose, such hoses usually have a supporting mesh in the form of a double spiral. Electrical wires are embedded in the spirals of the supporting mesh. By applying electric current to the first ends of the wires in the supporting mesh, and joining the second ends of the wires, the latter function as a heating wire in the casing of the hose. The hose casing and fluid media conveyed in the hose, such as air or oxygen, can consequently be heated.

In the case of the known solutions, the contacting of electrical wires on such hoses represents a significant problem. The electrical wires are thin and delicate so that they can be used as a heating wire. They can therefore be contacted mechanically with conductors of a supplied cable. The connecting and electrical contacting of the electrical conductors has been a manual task up until now. This is very complex, intensive in terms of time and staff, and expensive.

BRIEF SUMMARY

Embodiments of the present invention provide a connection device which simplifies the complex, manual, expensive and time-intensive contacting of the electrical conductors in the hose. It is intended to provide an option for connecting such electrical conductors which is more economical than the known solution.

Embodiments of the invention relate to a connection device which is formed from two half-shells joined to each other in a hinged fashion. The half-shells are provided so as to grip a hose and latch together on the hose. For this purpose, the half-shells are connected to each other in a hinged fashion on one side. The connection device can be placed around the hose by folding open the half-shells. The connection device is fastened and held on the hose by folding together the half-shells and latching them together on the side situated opposite the joint.

At least one catch, which engages in a catch socket on the second half-shell, is provided on one of the half-shells to latch together the half-shells. The catch and catch socket are provided on that side of the half-shell situated opposite the hinged joint.

The connection device has electrical contact elements which are provided both for contacting electrical conductors or wires of the hose and for contacting electrical conductors or wires of cables to be connected. It is thus provided to electrically join in each case one electrical conductor of the cable to be connected to an electrical conductor or wire of the hose.

The contact element is here fastened in one of the half-shells of the connection device and held in the latter. The contact element forms two contact regions. The contact regions are in each case provided for holding and contacting an electrical wire of the hose and an electrical wire of a cable to be connected. The contact regions can take different forms.

In one advantageous embodiment, a first one of the contact regions takes the form of an insulation displacement connector and is provided for contacting a wire of the hose. A second contact region of the contact element takes the form of a crimp connection and is provided for contacting a wire of the cable to be connected.

A further embodiment provides that both contact regions, the first contact region and the second contact region, of the contact element take the form of insulation displacement connectors. The first contact region is provided for contacting a wire of the hose, and the second contact region for contacting a wire of the cable to be connected.

The connection device provides conductor sockets in which the electrical wires of the hose and the electrical wires of the electrical conductor to be connected are held. The conductor sockets are preferably provided in the second half-shell and are situated in the region of the latching mechanism to the first half-shell.

When latching the two half-shells together, about the hose, the contact regions of the contact elements are inserted into contact openings in the second half-shell. The contact openings are provided in the second half-shell such that they cross the conductor sockets. By inserting the contact regions, designed as insulation displacement connectors, into the contact openings, the insulation displacement connectors electrically and mechanically contact the wires guided into the conductor sockets.

This advantageous embodiment enables simple placement of the connection device on the hose, and simultaneous secure contacting of the wires of the hose with the wires of a cable to be connected. Compared with the known possibility of contacting such hoses, the contacting to the proposed connection device is simpler, quicker, and hence more economical.

A further advantageous embodiment provides the formation of the conductor sockets in a separate pressure piece. The wires of the hose and of the cable to be connected are laid in these conductor sockets, and the pressure piece according to the above-described embodiment, is pressed onto the contact region of the contact element. The contact regions can thus engage in the contact openings, likewise present in the pressure piece, and electrically and mechanically contact the wires which are provided there.

BRIEF DESCRIPTION OF THE SEVERAL VIEWS OF THE DRAWINGS

Exemplary embodiments of the disclosure are shown in the drawings and are explained thereafter in detail. In the drawings.

DETAILED DESCRIPTION

The drawings contain partly simplified schematic views. In places, identical reference numerals have been used for elements that are the same but may not be identical. Different views of the same elements may be shown at different scales.

Figure 1:
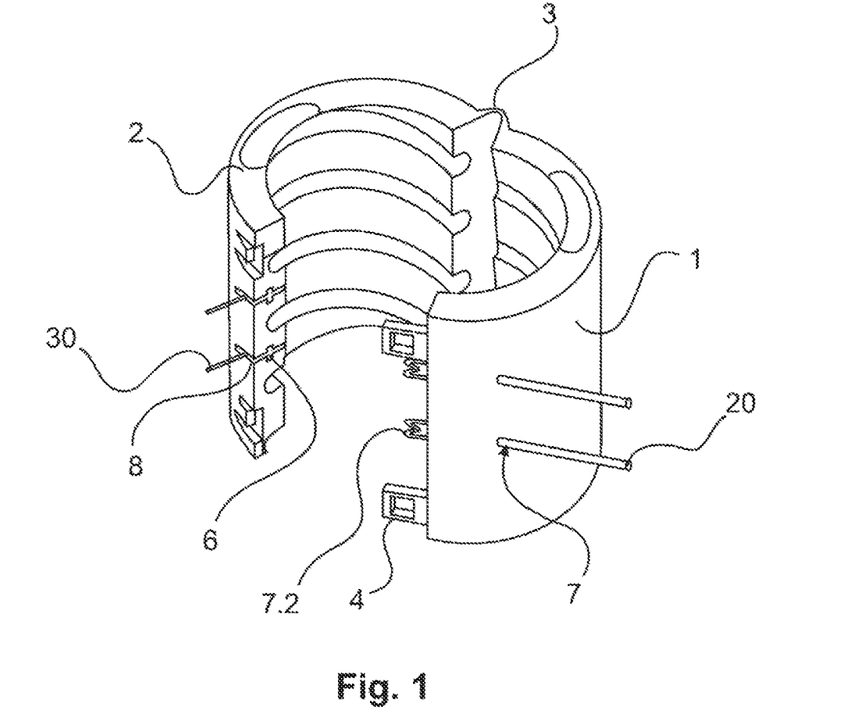
FIG. 1 shows a perspective view of a first connection device.

FIG. 1 shows a connection device in a perspective view. The connection device is formed from a first half-shell 1 and a second half-shell 2. The half-shells 1, 2 are joined to each other via a hinged joint 3 at their long sides.

Two catches 4 are provided at that side of the half-shells 2 which is situated opposite the joint 3. The catches 4 are designed to latch with corresponding catch sockets 5. By folding the first half-shell 1 and the second half-shell 2 together, the catches 4 can latch into the catch sockets 5 and thus close the connection device.

In addition, two electrical conductors 20 are connected on the first half-shell 1. The cables 20 are joined mechanically to the half-shell 1 by means of contact elements 7. The contact elements 7 have a first contact region 7.1 which, in this exemplary embodiment, is designed as a crimp terminal and contacts the conductors 20.

A second contact region 7.2 of the contact elements 7 is provided for contacting further electrical conductors 30. The second contact region 7.2 is here designed as an insulation displacement connector. The further electrical conductors 30 are arranged in conductor sockets 8 in the second half-shell 2. The conductor socket 8 is joined to a contact opening 6. The contact opening 6 is here provided as a cavity for receiving the second contact region 7.2.

By closing the two half-shells 1, 2 the second contact regions 7.2 dip into the contact openings 6 of the second half-shell 2. The further electrical conductors 30 situated in the conductor sockets 8 are contacted electrically by the insulation displacement connectors of the second contact regions 7.2.

Figure 2:
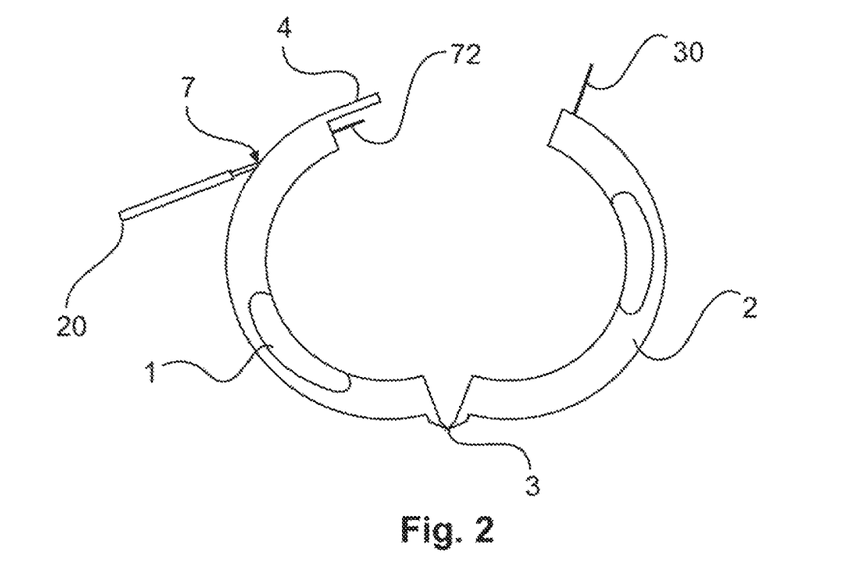
FIG. 2 shows a plan view of the first connection device.

FIG. 2 shows the connection device from FIG. 1 in a plan view. The first half-shell 1 and the second half-shell 2 can be seen. The contact element 7 is held in the first half-shell 1, wherein the second contact region 7.2 is oriented parallel to the catch 4 on the second half-shell 2. The further electrical conductor 30 is held in the second half-shell 2, perpendicular to the contact region 7.2 so as to be contacted by the latter.

Figure 3:
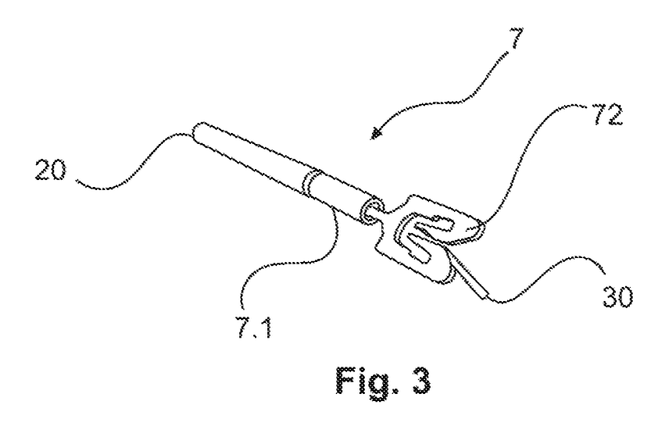
FIG. 3 shows a first contact element.

FIG. 3 shows an electrical contact element 7. It forms a first contact region 7.1 and a second contact region 7.2. The second contact region 7.2 is designed as an insulation displacement connector and contacts an electrical conductor 30. The first contact region 7.1 is designed as a crimp terminal and contacts an electrical conductor 20.

The connection device from FIGS. 1 and 2 is shown in FIG. 4, again in perspective. A hose 40 is additionally arranged in the connection device. The hose 40 has electrical conductors 30 which are arranged in the conductor sockets 8 of the second half-shell 2 in order to be contacted with the contact regions 7.2.

Figure 4:
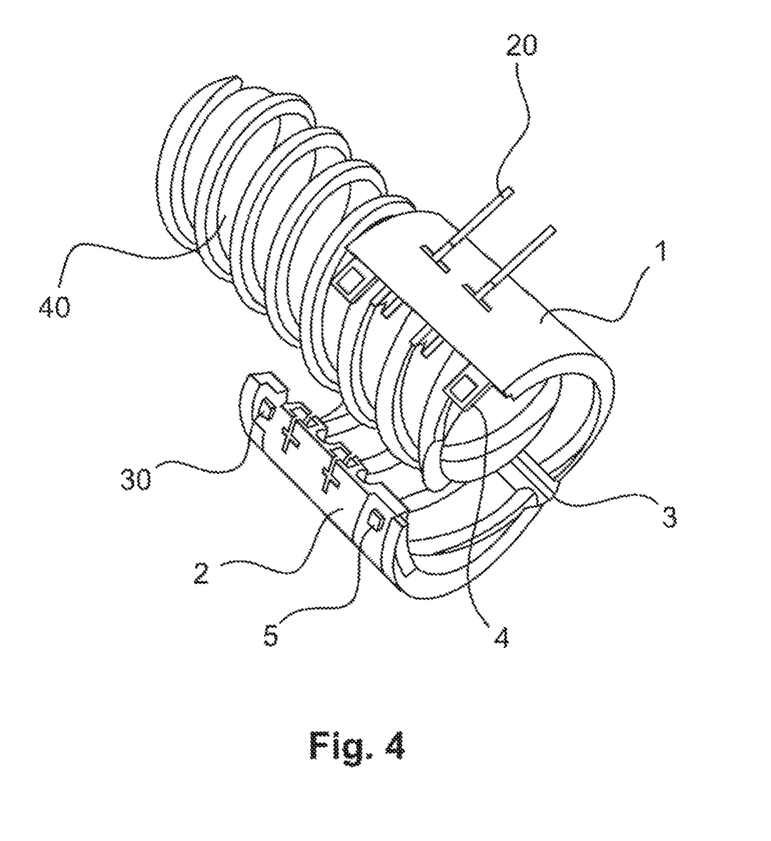
FIG. 4 shows a perspective view of the first connection device with a hose to be connected.
Figure 5:
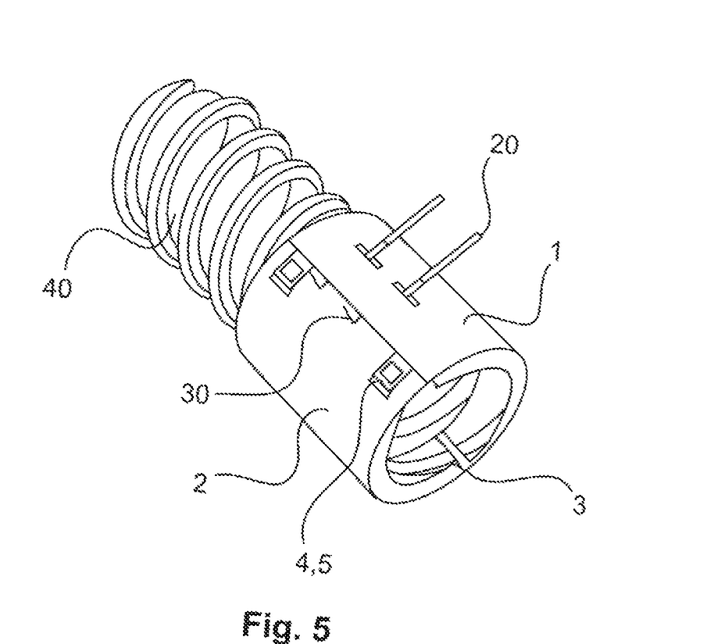
FIG. 5 shows a perspective view of the first connection device with a connected hose.
Figure 6:
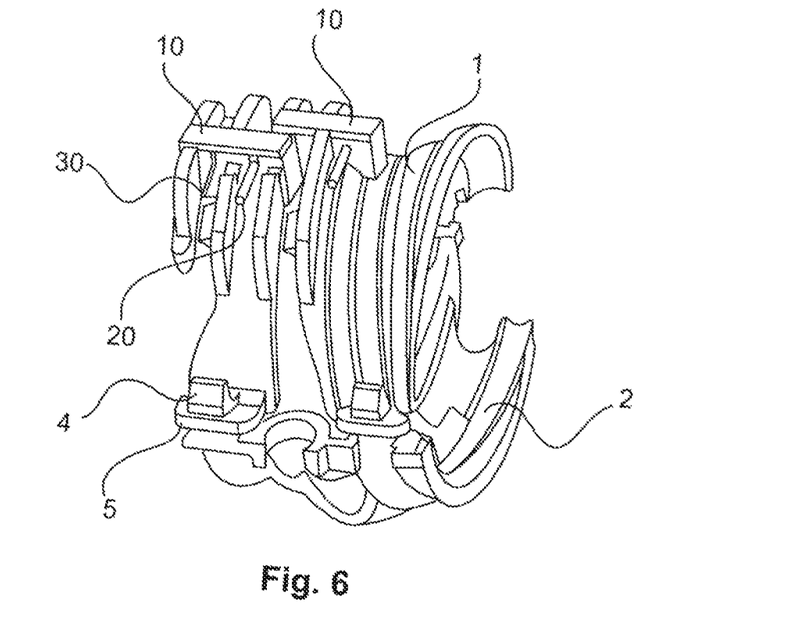
FIG. 6 shows a perspective view of the second connection device.
Figure 7:
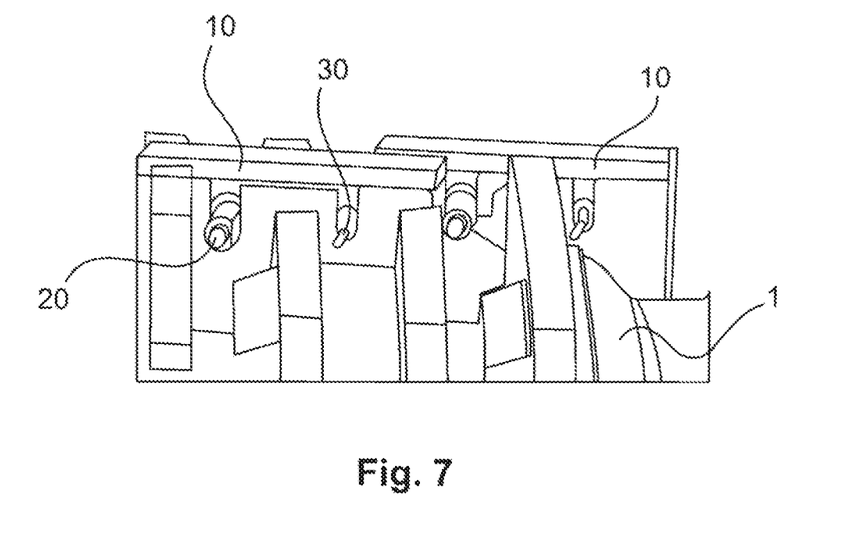
FIG. 7 shows a detailed perspective view of the second connection device.
Figure 8:
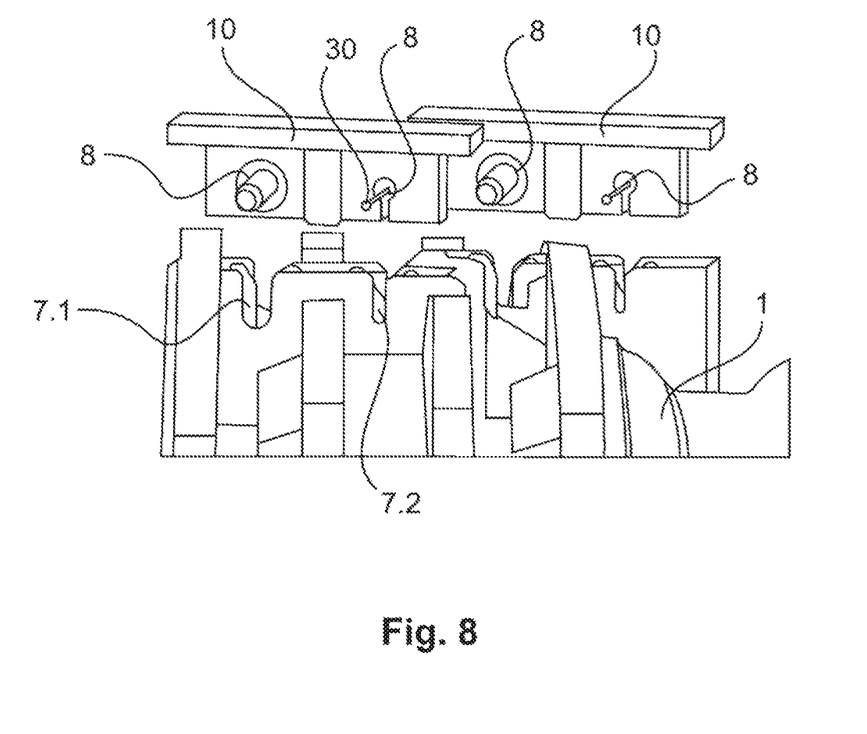
FIG. 8 shows a further detailed perspective view of the second connection device.
Figure 9:
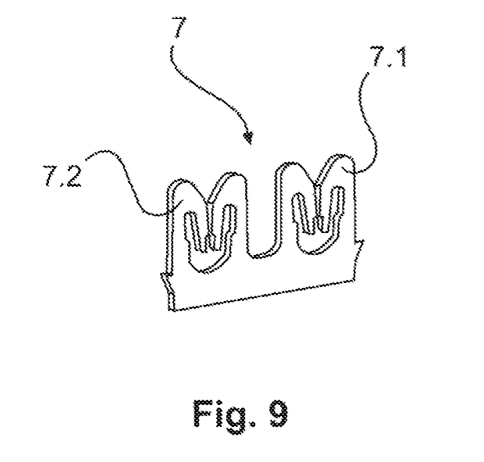
FIG. 9 shows a second contact element.
Figure 10:
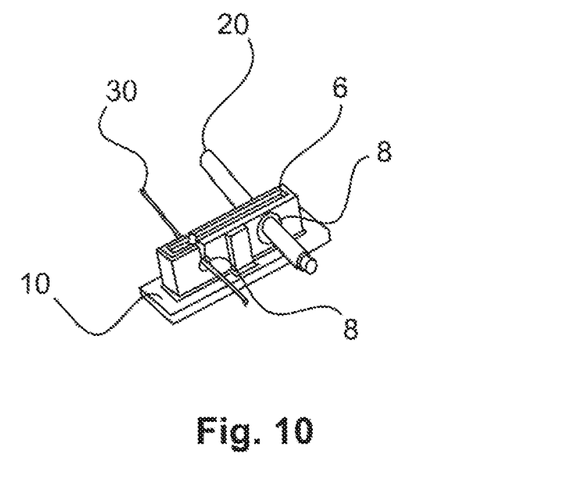
FIG. 10 shows a pressure piece of the second connection device with inserted electrical conductors.

FIG. 5 shows the arrangement from FIG. 4 but with the connection holder in the closed state. The two half-shells 1, 2 have been locked to each other and the electrical conductors 30 of the hose 40 brought into contact with the second contact regions 7.2 in the contact openings 6. The hose 40 is enclosed by the connection device. The connection device is fastened positively on the hose 40.

FIGS. 6 to 10 show a second exemplary embodiment of the invention. In this exemplary embodiment, the contact element 7 has two contact regions 7.1 and 7.2 which are designed as insulation displacement connectors. The contact element 7 is here held in the first half-shell 1. The electrical conductors 20, 30 are inserted into conductor sockets 8 of a pressure piece 10. The pressure piece 10 is designed as a separate component. As well as the conductor sockets 8, it has at least one contact opening 6. This serves to receive the contact regions 7.1, 7.2. The pressure piece 10 is pressed onto the contact regions 7.1, 7.2 of the contact element 7, as a result of which the contact regions 7.1 and 7.2 contact the conductors 20, 30 held in the pressure piece 10.

A further, third embodiment provides a combination of aspects of the exemplary embodiment of FIGS. 1 to 5 and aspects of the second exemplary embodiment of FIGS. 6 to 10. A contact element 7 with two contact regions 7.1, 7.2 designed as insulation displacement connectors is thus arranged such that, when the two half-shells 1, 2 are closed, the electrical conductors 20, 30 are pressed into the contact regions 7.1, 7.2. For this purpose, the electrical conductors 20, 30 are arranged in conductor sockets 8 in the second half-shell 2, and the contact element 7 in the first half-shell 1.

Figure 11:
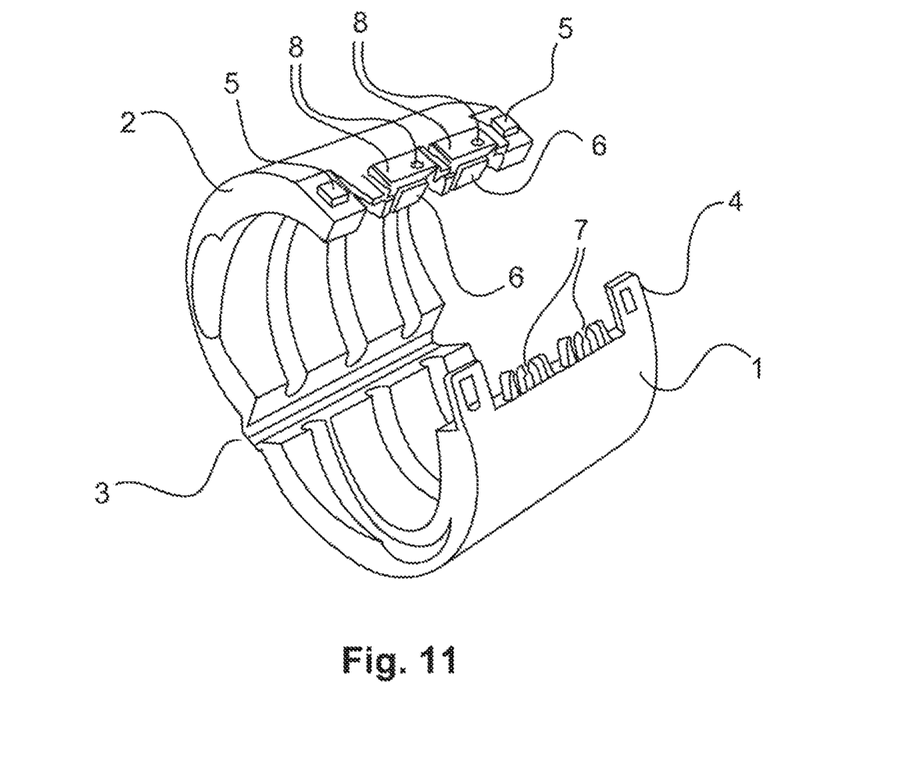
FIG. 11 shows a perspective view of a third connection device.
Figure 12:
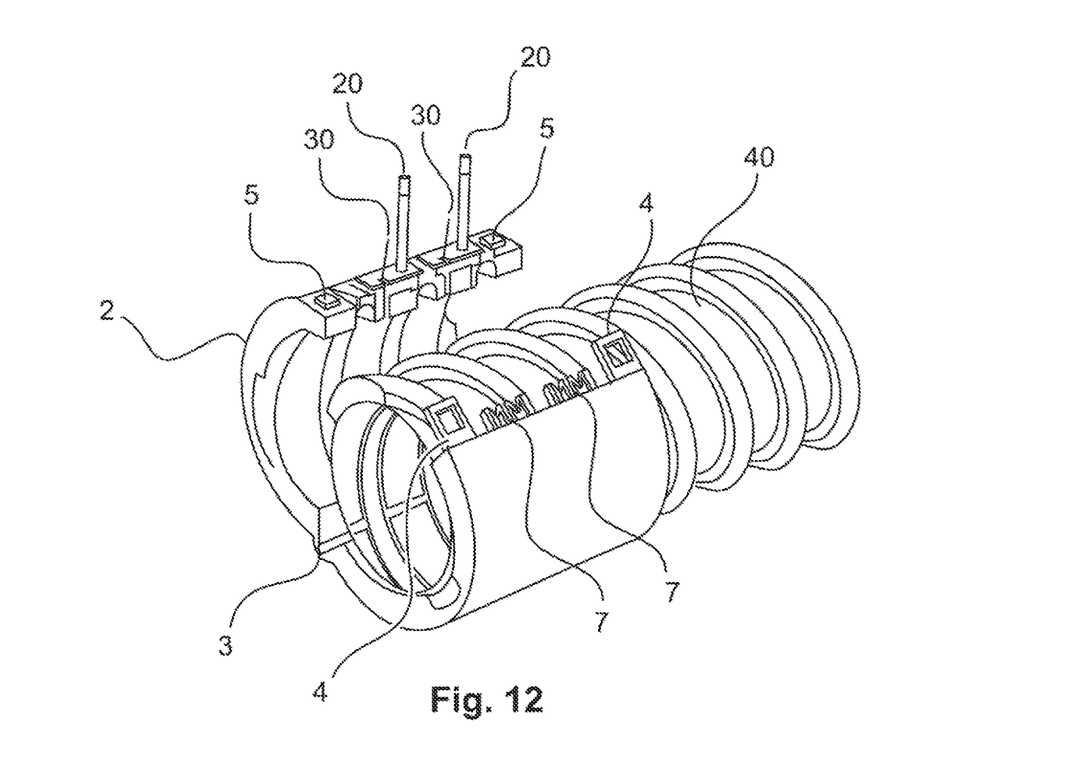
FIG. 12 shows a perspective view of the third connection device with a hose to be connected.
Figure 13:
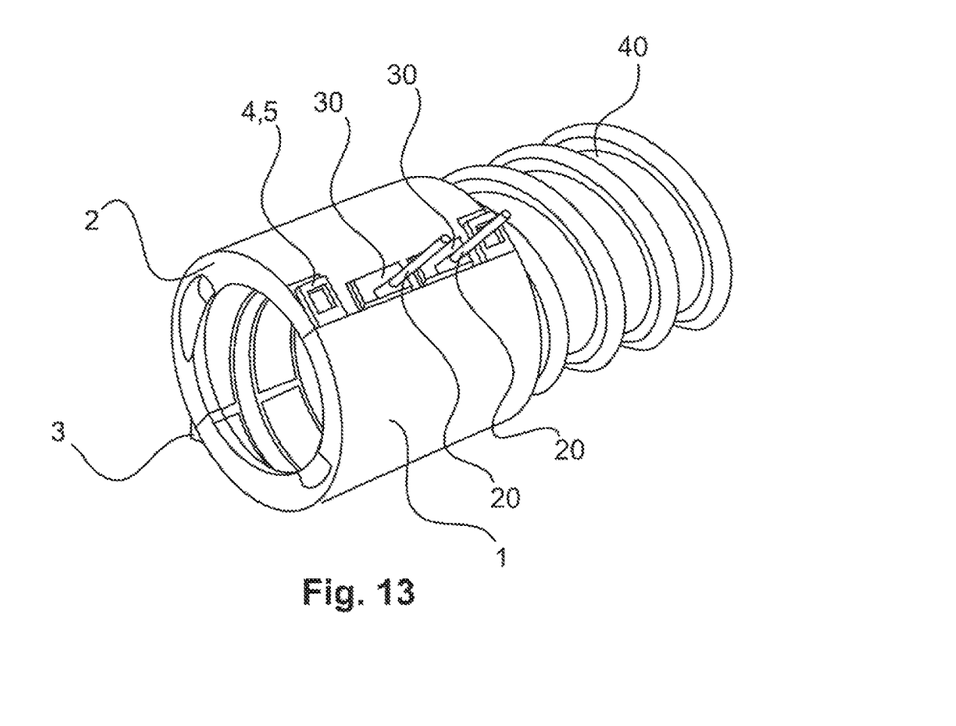
FIG. 13 shows a perspective view of the third connection device with a connected hose.

This third embodiment is shown in FIGS. 11 to 13. FIG. 11 shows a third connection device which is to a large extent the same as the connection device of FIGS. 1, 2, 4, 5. The contact elements 7 are, however, provided with two contact regions 7.1, 7.2 which are both designed as insulation displacement connectors. The contact regions 7.1, 7.2 are thus arranged in the separation region between the first half-shell 1 and the second half-shell 2 in such a way that they engage in the second half-shell 2 when the connection device is closed.

For this purpose, contact openings 6 are arranged in the second half-shell 2 such that the contact regions 7.1, 7.2 can engage in them. Conductor sockets 8 for receiving the electrical conductors 20, 30 extend transverse to the contact openings 6. The conductors 20, 30 can be inserted into the conductor sockets 8 and, when the connection device is closed, can be contacted with the contact regions 7.1, 7.2.

The third connection device, with a hose 40 placed in it, is shown in FIG. 12. The electrical conductors 30 of the hose, and the electrical conductors 20 of a cable to be connected are placed into the conductor sockets 8. When the connection device is closed, the catches 4 latch onto the catch sockets 5, as a result of which the connection device surrounds the hose 40 and is fastened to it.

At the same time, the contact regions 7.1, 7.2 of the contact elements 7 dip into the contact openings 6 in the second half-shell 2. The contact regions 7.1, 7.2 thus contact the electrical conductors 20, 30, which cross the contact openings 6. A simple and rapid fastening of the attachment device to the hose 40, with simultaneous electrical contacting of the electrical conductors 20, 30, is possible as a result of this special design.

In general, in the following claims, the terms used should not be construed to limit the claims to the specific embodiments disclosed in the specification and the claims, but should be construed to include all possible embodiments along with the full scope of equivalents to which such claims are entitled.

The invention claimed is:

1. A connection device for electrical cables, comprising a sleeve-like holding element and at least one contact element, wherein the sleeve-like holding element is formed from a first half-shell and a second half-shell, wherein the first half-shell and the second half-shell are joined to each other via a hinged joint, wherein the first half-shell and the second half-shell have a mutual locking device on a side situated opposite the hinged joint, wherein the locking device is formed from at least one catch and at least one catch socket corresponding to the catch, wherein the at least one contact element has two contact regions, a first contact region and a second contact region, wherein at least one conductor socket is formed in the second half-shell, wherein the conductor socket crosses a contact opening, wherein the contact element and the contact opening are arranged on that side of the first half-shell and the second half-shell which is situated opposite the hinged joint, in the region of the mutual locking device.

2. The connection device for electrical cables as claimed in claim 1, wherein the first contact region of the contact element is designed to contact a first type of electrical conductor, and in that the second contact region of the contact element is designed to contact a second type of electrical conductor.

3. The connection device for electrical cables as claimed in claim 1, wherein the second contact region is designed as an insulation displacement connector.

4. The connection device for electrical cables as claimed in claim 3, wherein the first contact region is designed as a crimp terminal.

5. The connection device for electrical cables as claimed in claim 3, wherein the first contact region and the second contact region are designed as insulation displacement connectors.

6. The connection device for electrical cables as claimed in claim 5, wherein the first contact region is designed for electrical cables with a larger diameter than the second contact region for electrical conductors with a smaller diameter.

7. The connection device for electrical cables as claimed in claim 1, wherein the contact element is held and fixed mechanically in the first half-shell.

8. The connection device for electrical cables as claimed in claim 1, wherein at least the second contact region of the contact element can dip into a contact opening of the second half-shell.

9. The connection device for electrical cables as claimed in claim 1, wherein the first contact region and the second contact region can dip into contact openings in the second half-shell.

10. The connection device for electrical cables as claimed in claim 1, wherein the contact element dips into the contact opening when the first and second half-shells are locked together.

11. The connection device for electrical cables as claimed in claim 1, wherein the connection device is designed for gripping a hose.

12. The connection device for electrical cables as claimed claim 11, wherein the hose is a hose for artificially supplying air to or ventilating patients in the field of medicine.

13. The connection device for electrical cables as claimed in claim 11, wherein the connection device for contacting two electrical conductors of the hose is provided with two supplied electrical conductors.

14. A system consisting of a hose and a connection device as claimed in claim 1, wherein the hose, at least in the region of the connection device, and the connection device are injection-molded with a polymer.

15. The system as claimed in claim 14, wherein the hose has two electrical conductors extending in parallel and spirally about the hose which are joined to the connection device.

* * * * *